United States Patent
Limonad et al.

(10) Patent No.: US 10,387,445 B2
(45) Date of Patent: Aug. 20, 2019

(54) HYBRID METHOD FOR ANOMALY CLASSIFICATION

(71) Applicant: International Business Machines Corporation, Armink, NY (US)

(72) Inventors: Lior Limonad, Nesher (IL); Nir Mashkif, Ein Carmel (IL); Segev E Wasserkrug, Haifa (IL); Alexander Zadorojniy, Haifa (IL); Sergey Zeltyn, Haifa (IL)

(73) Assignee: International Business Machines Corporation, Armonk, NY (US)

( * ) Notice: Subject to any disclaimer, the term of this patent is extended or adjusted under 35 U.S.C. 154(b) by 331 days.

(21) Appl. No.: 14/988,766

(22) Filed: Jan. 6, 2016

(65) Prior Publication Data

US 2017/0193078 A1   Jul. 6, 2017

(51) Int. Cl.
| | |
|---|---|
| G06F 16/26 | (2019.01) |
| G06F 21/55 | (2013.01) |
| H04L 29/06 | (2006.01) |
| G16H 50/70 | (2018.01) |
| G16H 50/20 | (2018.01) |
| G16H 30/40 | (2018.01) |

(52) U.S. Cl.
CPC ............ *G06F 16/26* (2019.01); *G06F 21/552* (2013.01); *G06F 21/554* (2013.01); *G16H 50/20* (2018.01); *G16H 50/70* (2018.01); *H04L 63/1425* (2013.01); *G16H 30/40* (2018.01)

(58) Field of Classification Search
CPC ......... G06F 17/30601; G06F 17/30572; G06F 16/26; G06F 21/554; G06F 21/552; G16H 50/20; G16H 30/40; G06H 50/70; H04L 63/1425

USPC ........................................................ 707/737
See application file for complete search history.

(56) References Cited

U.S. PATENT DOCUMENTS

| | | | |
|---|---|---|---|
| 7,668,843 B2 * | 2/2010 | Ertoz | G06F 21/552 706/20 |
| 7,792,770 B1 | 9/2010 | Phoha et al. | |
| 2013/0304710 A1 * | 11/2013 | Nachev | G06K 9/6284 707/690 |

FOREIGN PATENT DOCUMENTS

| | | |
|---|---|---|
| CA | 2845952 A1 | 3/2014 |
| CN | 103818744 A | 3/2014 |
| WO | 2012013920 A1 | 2/2012 |

OTHER PUBLICATIONS

Amer, Mennatallah, et al., "Enhancing One-class Support Vector Machines for Unsupervised Anomaly Detection", ODD '13, Chicago, IL, Aug. 11, 2013, pp. 8-15.*

(Continued)

*Primary Examiner* — Robert Stevens
(74) *Attorney, Agent, or Firm* — Barry Blount

(57) ABSTRACT

A computer implemented method, a computerized system and a computer program product for anomaly classification. The computer implemented method comprises obtaining a data set, wherein the data set comprises a plurality of data points. The method further comprises filtering the data set based on an absolute distance criterion and performing anomaly classification on a test data point of the data set, wherein the anomaly classification is based on a relative density criterion. The method further comprises outputting an outcome of the anomaly classification.

13 Claims, 3 Drawing Sheets

(56) References Cited

OTHER PUBLICATIONS de Vries, Timothy, et al., "Finding Local Anomalies in Very High Dimensional Space", ICDM 2010, Sydney, NSW, Australia, Dec. 13-17, 2010 pp. 128-137.*
Pei, Yaling, et al., "An Efficient Reference-based Approach to Outlier Detection in Large Datasets", ICDM '06, Hong Kong, China, Dec. 18-22, 2006, pp. 478-487.*
Liu, Qing-Bao, et al., "Relative Density Based K-Nearest Neighbors Clustering Algorithm", Proc. of the 2nd International Conf. on Machine Learning and Cybernetics, Xi'an, China, Nov. 2-5, 2003, pp. 133-137.*
Jones, M. Tim, "Unsupervised learning for data classification", IBM developerWorks, published Dec. 4, 2017, downloaded from: www.ibm.com/developerworks/library/cc-unsupervised-learning-data-classification/index.html, pp. 1-19.*
Roshni dubey et al., "KNN based Classifier Systems for Intrusion Detection", International Journal of Advanced Computer Technology | vol. 2, No. 4, 2013, 5 pages.
Mennatallah Amer et al., "Nearest-Neighbor and Clustering based Anomaly Detection Algorithms for RapidMiner", Conference: Proceedings of the 3rd RapidMiner Community Meeting and Conferernce (RCOMM 2012), 12 pages.
Timothy de Vries et al., "Density-preserving projections for large-scale local anomaly detection", : Regular Paper Knowledge and Information Systems Jul. 2012, vol. 32, Issue 1, pp. 25-52, 28 pages.
Lou, Chen et al., "Local density-based anomaly detection in hyperspectral image", J, Appl. Remote Sens. 9(1), 095070 (Jul. 15, 2015). DOI:10.1117/1.JRS.9.095070, Published 2015, History Received Nov. 12, 2014; Accepted May 21, 2015. Abstract, 1 page.

\* cited by examiner

HYBRID METHOD FOR ANOMALY CLASSIFICATION

TECHNICAL FIELD

The present disclosure relates to anomaly classification and detection in general, and to anomaly classification based on absolute distance and relative density, in particular.

BACKGROUND

Anomaly detection refers to identification of items, events or observations, which do not conform to an expected pattern or other items in a dataset. Typically, anomalous items may indicate a problem. As an example, anomalous items in a medical test results may indicate medical problems.

Anomaly detection may be applicable in a variety of domains, such as intrusion detection for cyber-security, fraud detection for credit cards, fault detection in safety critical systems, health system monitoring, event detection in sensor networks, detecting Eco-system disturbances, or the like.

BRIEF SUMMARY

One exemplary embodiment of the disclosed subject matter is a computer-implemented method comprising obtaining a data set, wherein the data set comprises a plurality of data points. The method further comprising filtering the data set based on an absolute distance criterion, performing anomaly classification on a test data point of the data set, wherein the anomaly classification is based on a relative density criterion; and outputting an outcome of the anomaly classification.

Another exemplary embodiment of the disclosed subject matter is a computerized apparatus having a processor, the processor being adapted to perform the steps of: obtaining a data set, wherein the data set comprises a plurality of data points; filtering the data set based on an absolute distance criterion; performing anomaly classification on a test data point of the data set, wherein the anomaly classification is based on a relative density criterion; and outputting an outcome of the anomaly classification.

Yet another exemplary embodiment of the disclosed subject matter is a computer program product comprising a computer readable storage medium retaining program instructions, which program instructions when read by a processor, cause the processor to perform a method comprising: obtaining a data set, wherein the data set comprises a plurality of data points; filtering the data set based on an absolute distance criterion; performing anomaly classification on a test data point of the data set, wherein the anomaly classification is based on a relative density criterion; and outputting an outcome of the anomaly classification.

THE BRIEF DESCRIPTION OF THE SEVERAL VIEWS OF THE DRAWINGS

The present disclosed subject matter will be understood and appreciated more fully from the following detailed description taken in conjunction with the drawings in which corresponding or like numerals or characters indicate corresponding or like components. Unless indicated otherwise, the drawings provide exemplary embodiments or aspects of the disclosure and do not limit the scope of the disclosure. In the drawings.

DETAILED DESCRIPTION

Figure 1A:
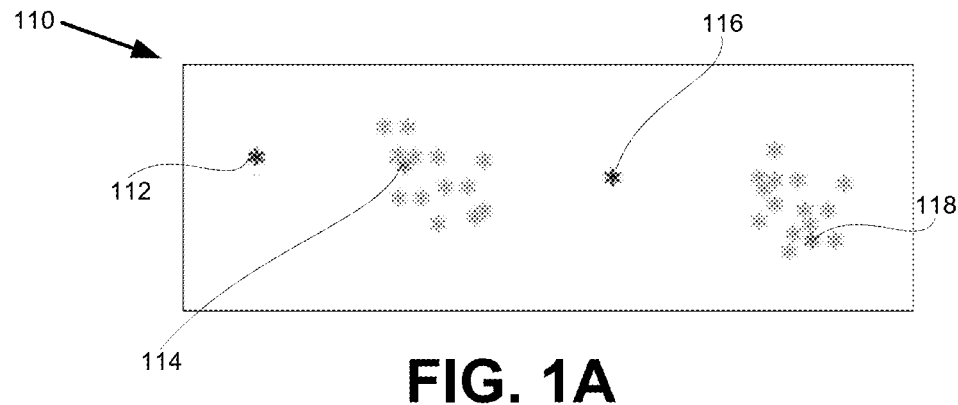
FIGS. 1A-1C show schematic illustrations of anomaly classification problems, in accordance with some exemplary embodiments of the subject matter.

One technical problem dealt with by the disclosed subject matter is to provide for an efficient manner to perform an anomaly classification.

Automatic anomaly classification may be an important problem, as anomalies in data may indicate a significant actionable information in a wide variety of application domains. As an example, an anomalous traffic pattern in a computer network may indicate that a hacked computer is sending out sensitive data to an unauthorized destination. As another example, an anomalous MRI image may indicate the presence of malignant tumors.

Some anomaly classification methods may be based on the assumption that normal data instances occur in dense neighborhoods, while anomalies occur far from their closest neighbors. Such anomaly classification techniques may classify points as anomalies if they correspond to a low local density. Such classification technique may be used for unsupervised data, may not require any assumptions regarding generative distribution for the data, and may be purely data driven. There may be several families of anomaly classification techniques that are based on density measurements: a first family may include techniques that use absolute distance of data instances to compute anomaly score, and a second family may include techniques that compute relative density of each data instance to compute its anomaly score.

Techniques that use absolute distance of data instances to compute anomaly score may classify as anomalies data instances whose distance from their neighbors is larger than typical distance from neighbors in a given data set. $k^{th}$ Nearest Neighbor (KNN) may be one method of this kind: a distance from neighbors may be defined as its absolute distance to its $k^{th}$ nearest neighbor in a given data set. In some exemplary embodiments, hypergraph-based techniques may also be based on absolute distance. A hypergraph-based technique may enable incorporation of categorical attributes of the data points in the data set. Variety of extensions may be added to these techniques, such as using different distance measures to handle different data types, modifying the definition of the anomaly score, or the like. However, such techniques may perform poorly if normal data has areas of varying densities. In this case, data points with the same distance from neighbors may be either anomalous or normal, depending on their location.

Techniques that compute relative density may classify as anomalies data instances local density that is significantly lower than local density of their neighbors. Local Outlier Factor (LOF) may be a method of this kind. However, relative density based techniques may perform poorly if the data has regions containing outliers with similar relative density to normal data inside the region, or if the data has outlier regions with uniform density. In such a case, data points with similar relative density may be either anomalous or normal, depending on their location.

One technical solution is to provide for a hybrid method which combines both the absolute distance criterion and the relative density criterion. Techniques based on absolute distance of data instances may be used to filter a given data set, and techniques based on relative density may be used to perform anomaly classification on a test data point of the given data set after being filtered, or an anomaly detection on the data set.

In some exemplary embodiments, a data set comprising a plurality of data points and a test data point of the data set may be obtained. Each data point may represent a pattern, an event, an observation, or the like. Each data point may be described using a set of attributes.

In some exemplary embodiments, the data set may be normalized to enable independence of anomaly detection of specific measurements units of attributes of the data points.

In some exemplary embodiments, the data set may be filtered based on an absolute distance criterion, such as based on the KNN technique, hypergraph-based techniques, or the like. In some exemplary embodiments, the absolute distance criterion may be having a ratio between a distance measurement and a statistical average of distance measurements of other data points in the data set, above a filtering threshold. Filtering the data set may be performed by computing a statistical average of absolute distances of all data points in the data set from their respective $k^{th}$ nearest neighbor. In the present disclosure the term "statistical average" of absolute distances includes any of the following: an arithmetic mean of the absolute distances, a median of the absolute distances, a mode of the absolute distances, or the like. A data point may be filtered if the ratio between a distance measurement and the statistical average is above the filtering threshold. The distance measurement may be an absolute distance between the filtered data point and its respective $k^{th}$ nearest neighbor.

After filtering the data set, anomaly classification may be performed to classify a test data point. The anomaly classification may be based on a relative density criterion. The anomaly classification may be performed by computing a relative density measurement of the test data point. In some exemplary embodiments, the relative density measurement may be a number of data points of the filtered data set, which the test data point is one of their respective k nearest neighbors. The test data point may be determined abnormal if the relative density measurement is below a density threshold.

In some exemplary embodiments, the relative density criterion may be based on the LOF algorithm, an Outlier Detection using Indegree Number (ODIN) algorithm, a Connectivity Based Outlier Factor algorithm, or the like.

One technical effect of utilizing the disclosed subject matter is enhancing the anomaly detection in problematic data sets, such as data having regions of varying densities, data having regions of varying distances, data having outliers with uniform relative density, or the like. Filtering the data set according to absolute distance criterion may clean the data set from distant data points that may severely affect performance of the anomaly detection that makes use of the relative density criterion.

Another technical effect of utilizing the disclosed subject matter is to provide for a potentially better anomaly classification, with potentially more accurate results than was previously known.

Figure 1B:
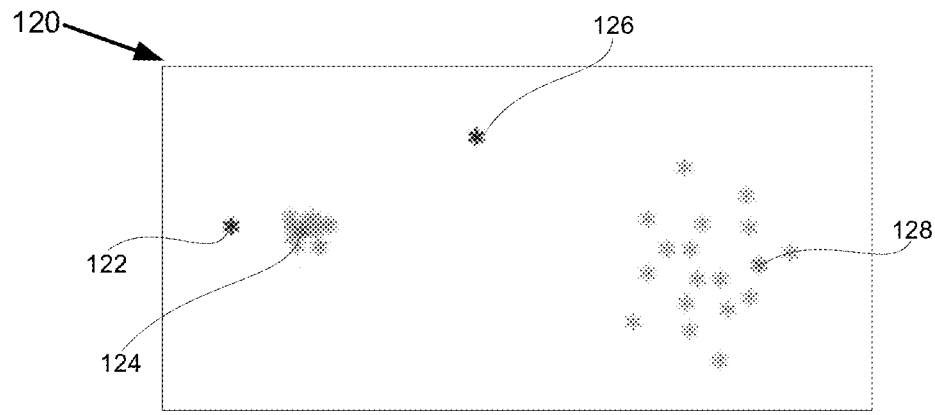
Figure 1C:
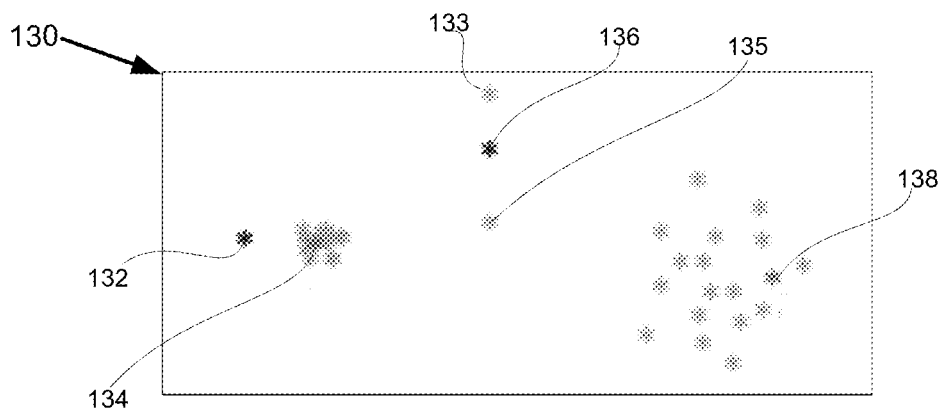

Referring now to FIGS. 1A-1C showing schematic illustrations of anomaly classification problems, in accordance with some exemplary embodiments of the subject matter.

FIG. 1A illustrates an example of an anomaly classification problem that may be solved appropriately by a technique that uses distance of data instances to detect anomaly, such as for example KNN. Additionally or alternatively, the anomaly classification problem of FIG. 1A may also be solved using relative density technique, such as for example LOF.

Data Set 110 may be exemplified as a 2-dimensional data set, however the disclosed subject matter is not limited to a particular dimension. Data Set 110 may comprise a plurality of data points. Each data point may represent a data instance such as an object, a record, a point, a vector, a pattern, an event, a case, a sample, an observation, an entity, or the like. The data points may be described using a set of fields, such as binary fields, categorical fields, continuous fields, a combination thereof, or other data types fields. Additionally or alternatively, the data points may consist of a single attribute representing the data.

In some exemplary embodiments, Data Set 110 may be an unsupervised data set. Unsupervised data set may consist of unlabeled data points, i.e. the data points in the data set may not be labeled as normal or anomalous. It may be assumed that the majority of data points in the unsupervised data set are normal and based on such assumption abnormal data points may be detected.

Test Data Point 112, Test Data Point 114, Test Data Point 116, and Test Data Point 118 may be data points to be classified. The test data points may be classified as normal or anomalous comparing with a remainder of the data set. Anomalies may be data points that do not conform with a notion of a majority of the data points in Data Set 110.

In some exemplary embodiments, the test data points may be classified using a technique that is based on an absolute distance criterion. In some exemplary embodiments, the absolute distance criterion may be having a ratio between an absolute distance measurement and a statistical average of absolute distance measurements of all data points in Data Set 110 from their respective $k^{th}$ nearest neighbor, that is above a filtering threshold.

The technique that is based on an absolute distance criterion may correctly classify Test Data Point 112 and Test Data Point 116 as anomalies. Test Data Point 114 and Test Data Point 118 may be correctly classified as normal.

In other exemplary embodiments, the test data points may be classified using a density-based technique which relies on a relative density criterion. In some exemplary embodiments, the relative density criterion may be having a relative density measurement below a density threshold. In some exemplary embodiments, the relative density measurement may be a number of data points of Data Set 110 which the test data point is one of their respective k nearest neighbors.

The density-based approach may correctly classify Test Data Point 112 and Test Data Point 116 as anomalies. While Test Data Point 114 and Test Data Point 118 may be correctly classified as normal.

FIG. 1B shows a schematic illustration of anomaly classification problem that may be solved appropriately by a technique that uses relative density to detect anomaly, such as for example an LOF approach. However, such problem may not be solved properly by a technique that uses distances of data instances to detect anomaly, such as for example, KNN approach.

In some exemplary embodiments, Data Set 120 may comprise a plurality of data points and a plurality of test data points such as Test Data Point 122, Test Data Point 124, Test Data Point 126 and Test Data Point 128.

As can be apparent to a person viewing the illustration of Data Set 120, Test Data Point 122 is anomalous, and Test Data Point 128 is normal. However, the distance of Test Data Point 122 from its neighbors and the distance of Test Data Point 128 from s its neighbors are similar. Using an absolute distance approach, Test Data Point 122 and Test Data Point 128 may be both classified as normal. Accordingly, approaches that use absolute distance of data instances to detect anomaly may not function optimally in data sets similar to Data Set 120.

Approaches that are based on relative density may correctly classify Test Data Point 124 and Test Data Point 128 as normal, and Test Data Point 122 and Test Data Point 126 as anomalous. Test Data Point 122 and Test Data Point 126 may have a low local density as there are no other data points in their neighborhood. Test Data Point 124 and Test Data Point 128 have local densities uniformly with densities of their neighborhoods, and therefore may be correctly classified as normal.

Referring now to FIG. 1C showing a schematic illustration of anomaly classification problem with a data set containing outliers. A Data Set 130 may comprise a plurality of data points and a plurality of test data points such as Test Data Point 132, Test Data Point 134, Test Data Point 136 and Test Data Point 138.

In some exemplary embodiments, Data Set 130 may contain outliers, such as Data Point 133 and Data Point 135.

Relative density based approaches may classify anomalous Test Data Point 136 as normal, as its relative density is similar to the density of its neighbors, Data Point 133 and Data Point 135 in Data Set 130.

Distance-based approaches, such as KNN, may also incorrectly classify test points of Data Set 130. For example, and similarly to Test Data Point 122, Test Data Point 132 may be incorrectly classified as normal.

In accordance with the disclosed subject matter, applying a hybrid approach may correctly classify Data Set 130. During the hybrid approach, Data Set 130 may be filtered based on an absolute distance criterion. During such filtering, Data Point 133 and Data Point 135 may be eliminated from the data set. As a result, the filtered data set may be similar to Data Set 120, which may be correctly classified using anomaly classification which is based on relative density criterion, such as LOF.

In some exemplary embodiments, in order to avoid filtering test data points that are to be classified, the data set that is being filtered may exclude test data points (e.g., 132, 134, 136, 138) and such test data points may be added to the filtered data set before classification. In some exemplary embodiments, each test data point may be added independently when being classified so as to avoid being affected by anomalous test data points.

Figure 2:
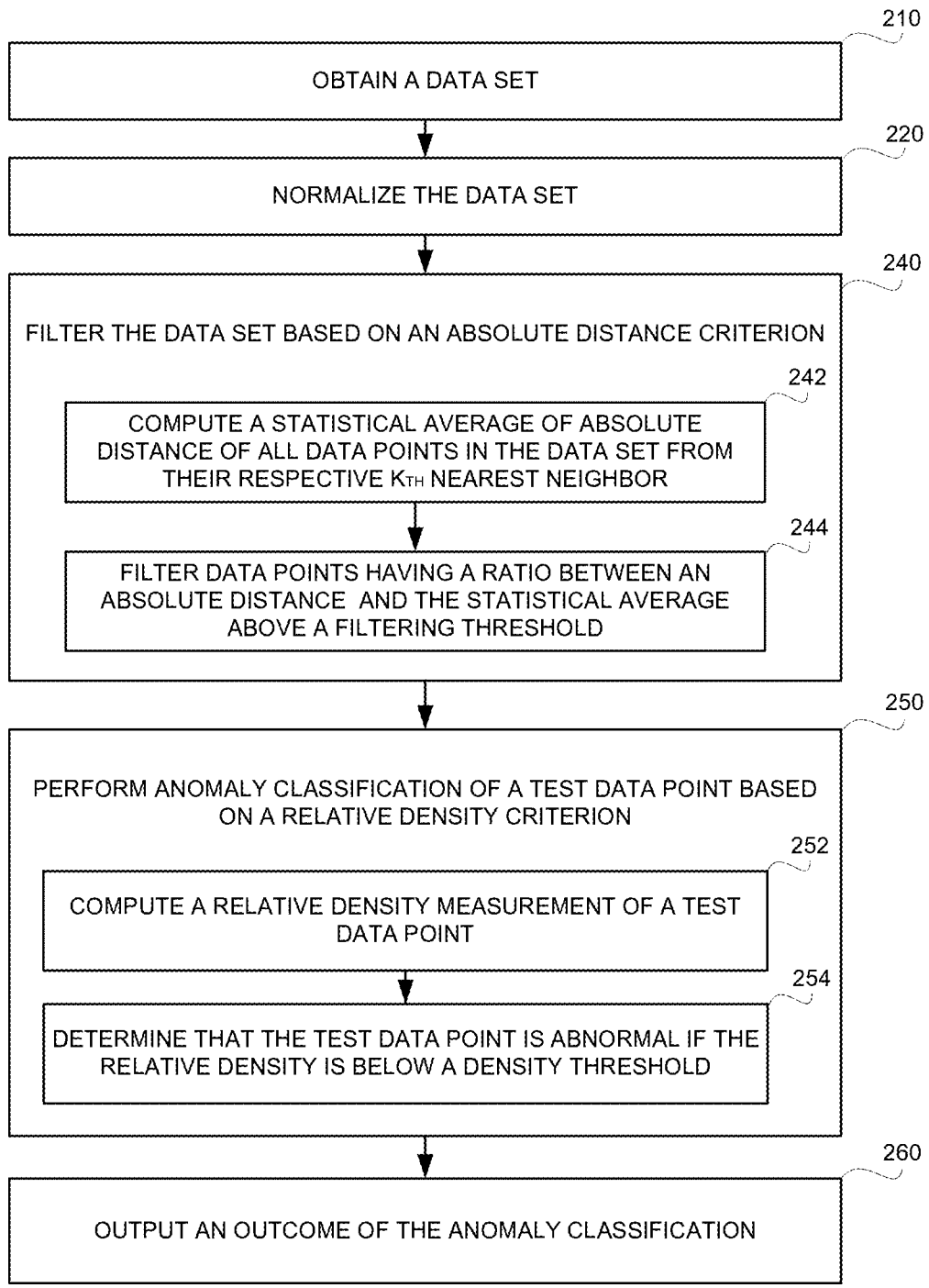
FIG. 2 shows a flowchart diagram of a method, in accordance with some exemplary embodiments of the subject matter.

Referring now to FIG. 2 showing a flowchart diagram of a method, in accordance with some exemplary embodiments of the subject matter.

In Step 210, a data set may be obtained. The data set may comprise a plurality of data points. As an example, in an anomaly detection for credit card fraud detection, the data set may comprise credit card transactions. Each data point may correspond to an individual's credit card transaction. Each data point may be described using a single feature, such as amount spent in the transaction, or using several features, such as amount spent in the transaction, date and time of purchase, location of the transaction, or the like. As another non-limiting example, the data set may be a medical data set describing medical situations, such as a description of a tissue, where the anomaly detection is used for tumor detection. Each data point may describe a medical image of a tissue, such as an ultrasonic image, computed tomography (CT) scan, magnetic resonance imaging (MRI) scan, or the like. The medical image may be described using a vector of values describing features of the medical image, such as boundaries of the tissue, shape of the tissue or the like.

In Step 220, the data set may be normalized. In some exemplary embodiments, the data set may be normalized to allow comparison of the data points, such as by adjusting scales of measurements of the data points, scaling data to smaller intervals, or the like. Units of measurement of the data points may be eliminated by transforming the data into new values with a mean of zero (0) and a standard deviation of one (1).

In Step 240, the data set may be filtered based on an absolute distance criterion. In some exemplary embodiments, a KNN based algorithm may be used for filtering the data set. The KNN based algorithm may be used to set a filtering criterion based on the distance of a data point to its $k^{th}$ nearest neighbor in the data set. Additionally or alternatively, a data point may be classified by a majority vote of its neighbors in the dataset, with the data point being assigned to a class most common among its k nearest neighbors. In some exemplary embodiments, k may be a positive integer. A small value of k may mean that noise in the data set will have a higher influence on the filtering. A large value may reduce the overall noise, however, it may make computations of the $k^{th}$ nearest neighbors computationally expensive. In some exemplary embodiments, the value of k may be between 1 and 10. In some exemplary embodiments, k may be selected based on the number of the data points in the data set, for example, k may be selected to be a square root of the number of data points in the data set.

In some exemplary embodiments, the absolute distance criterion may use a similarity measurement as a distance measurement. Additionally or alternatively, the absolute distance criterion may be based on different distance measures to handle different data types, such as Euclidean distance, Manhattan distance, Minkowski distance, Hamming distance, or the like.

As may now be appreciated, filtering may be based on a variety of different absolute distance criteria. Non-limiting examples are provided hereinbelow. Filtering a data point may be based on hypergraph-based criterion. Additionally or alternatively, Filtering a data point may be based on a sum of distances from its k nearest neighbors, a number of nearest neighbors that are not more than a predetermined distance threshold apart from the data point, or the like. Additionally or alternatively, a data point may be filtered based on a ratio between an absolute distance of the data point from its $k^{th}$ nearest neighbor and a statistical average of absolute distances of all data points from their respective $k^{th}$ nearest neighbor in the data set.

In Step 242, a statistical average of absolute distances of all data points from their respective $k^{th}$ nearest neighbor in the data set may be computed. In some exemplary embodiments, an absolute distance of a data point from its $k^{th}$ nearest neighbor in the data set may be the Euclidean distance between the data point and its $k^{th}$ nearest neighbor in the data set. In some exemplary embodiment, the statistical average may be used to provide a measurement that is indicative of a central value in the data set. The statistical average may be, but is not limited to, mean, median, mode, range, or other central or typical value.

In Step 244, data points having a ratio between an absolute distance and the statistical average above a filtering threshold may be filtered. In some exemplary embodiments, the filtering threshold may be predetermined by a user. Additionally or alternatively, the filtering threshold may be determined based on the data set, for example based on an average distance between data points in the data set, an average distance between data points in predetermined normal regions of the data set, based on the number of data points in the data set, or the like. In some exemplary embodiments, the filtering threshold may be determined such that the number of filtered data points do not exceed a predetermined percentage of the data set, such as for example about 1%, about 2%, about 3%, about 5%, or the like.

In Step 250, an anomaly classification may be performed on a test data point based on a relative density criterion. In some exemplary embodiments, relative density based anomaly detection may estimate a density of a neighborhood of each data point in the data set. A data point that lies in a neighborhood with low density may be classified as anomalous, while a data point that lies in a dense neighborhood may be classified as normal. A relative density may be a density of a data point relative to a density of its neighborhood. Different density measures may be used, by differently defining a neighborhood of a data points, by considering what neighbor data points to include in the density measure, or the like.

In some exemplary embodiments, the relative density criterion may be determined using density based algorithms, such as LOF, Density-Based Spatial Clustering of Applications with Noise (DBSCAN), Ordering Points To Identify the Clustering Structure (OPTICS), or the like.

In some exemplary embodiments, a test data point may be obtained to be classified for anomaly. In some exemplary embodiments, the test data point may be a part of the data set. In some cases, the test data point may be filtered from the data set in Step 240 or removed therefrom prior to such filtering. In such cases, the test data point may be added to the data set for the purpose of performing the anomaly classification.

In some exemplary embodiments, there may be a test set comprising a plurality of test data points to be classified based on the data set. The data set may be filtered independently from the test set. In some exemplary embodiments, during classification of each test data point of the test set, each such point is considered in conjunction with the data set and without considering the remainder of the test set.

In Step 252, a relative density measurement of the test data point may be computed. In some exemplary embodiments, the relative density of a data point may be a ratio between a local density of the data point and a local density of a neighborhood of the data point. The neighborhood of the data point based on the k nearest neighbors of the data point. The local density of the neighborhood of the data point may be the average local density of the k nearest neighbors of the data point.

In some exemplary embodiments, a distance of a data point to the $k^{th}$ nearest neighbor may be an estimate of the inverse of the relative density of the data point. The distance of the data point to the $k^{th}$ nearest neighbor may be equivalent to a radius of a hyper-sphere, centered at the data point, which contains k other data points. Accordingly, the relative density measurement may be a number of data points of the data set, which the test data point is one of their respective k nearest neighbors. In some exemplary embodiments, k may be a parameter of the density measurement method. Additionally or alternatively, k may be defined by the user, or set by default to a value of 10, 20, a number smaller than the square root of the number of data points in the data set, or the like.

In Step 254, the test data point is determined to be abnormal if the relative density measurement is below a density threshold. The density threshold may be a control parameter of the method, predetermined by a user, or computed based on the data set.

In Step 260, an outcome of the anomaly classification may be outputted. In some exemplary embodiments, the outcome may contain a classification of the test data point as normal or anomalous. Additionally or alternatively, the outcome may comprise classifications of plurality of test data points, such as comprised by a test set.

Figure 3:
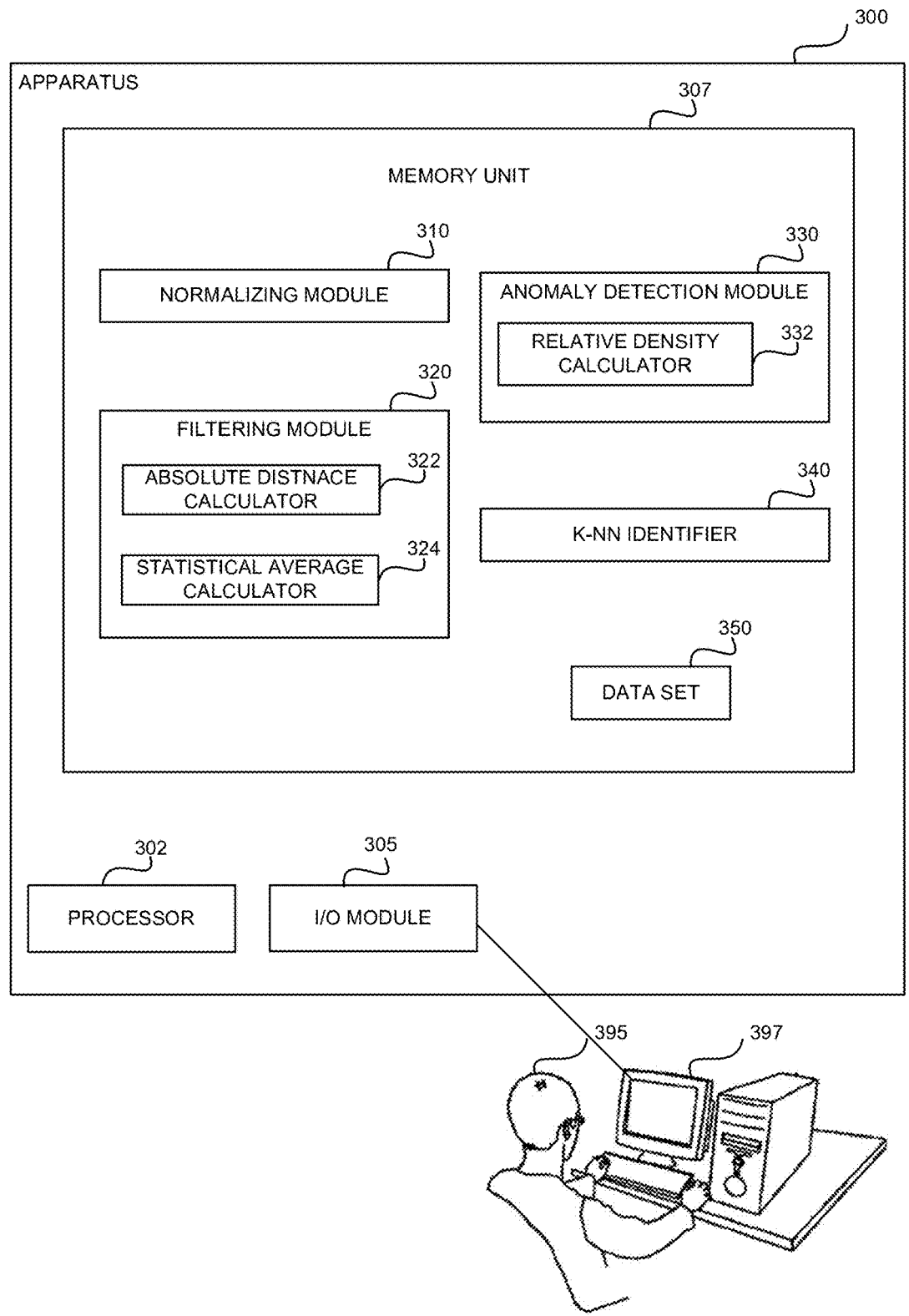
FIG. 3 shows a block diagram of an apparatus, in accordance with some exemplary embodiments of the disclosed subject matter.

Referring now to FIG. 3 showing an apparatus in accordance with some exemplary embodiments of the disclosed subject matter.

In some exemplary embodiments, Apparatus 300 may comprise one or more Processor(s) 302. Processor 302 may be a Central Processing Unit (CPU), a microprocessor, an electronic circuit, an Integrated Circuit (IC) or the like. Processor 302 may be utilized to perform computations required by Apparatus 300 or any of it subcomponents.

In some exemplary embodiments of the disclosed subject matter, Apparatus 300 may comprise an Input/Output (I/O) Module 305. Apparatus 300 may utilize I/O Module 305 as an interface to transmit and/or receive information and instructions between Apparatus 300 and external I/O devices, such as a Workstation 397, a Computerized Device (not shown), or the like.

In some exemplary embodiments, I/O Module 305 may be used to provide an interface to a User 395 of the system, such as by providing output, outcome of anomaly detection, or the like. User 395 may use Workstation 397 to input data sets to be detected for anomaly, test data point to be classified as normal or anomalous, test data sets, or the like. It will be appreciated that Apparatus 300 can operate without human operation.

In some exemplary embodiments, Apparatus 300 may comprise a Memory Unit 307. Memory Unit 307 may be a hard disk drive, a Flash disk, a Random Access Memory (RAM), a memory chip, or the like. In some exemplary embodiments, Memory Unit 307 may retain program code operative to cause Processor 302 to perform acts associated with any of the subcomponents of Apparatus 300.

In some exemplary embodiments, Memory Unit 307 may retain a Data Set 350. In some exemplary embodiments, some data instances of Data Set 350 may be labeled as normal or anomalies. Additionally or alternatively, there may be no labeling.

In some exemplary embodiments, Memory Unit 307 may comprise a Normalizing Module 310. Normalizing Module 310 may be configured to normalize a data set, such as Data Set 350. Normalizing Module 310 may be configured to adjust values of the data instances of Data Set 350 to allow comparison of corresponding normalized values independently from differences of measuring units, to avoid bias towards a particular pattern of data instances, or the like.

In some exemplary embodiments, Memory Unit 307 may comprise a Filtering Module 320. Filtering Module 320 may be configured to filter a data set, such as Data Set 350 from outliers that may adversely affect the anomaly classification process. In some exemplary embodiments, Filtering Module 320 may be configured to filter Data Set 350 based on an absolute distance criterion, such as using based on KNN. In some exemplary embodiments, Filtering Module 320 may filter data instances from Data Set 350 based on a filtering threshold, which may be set manually, determined automatically, or the like.

In some exemplary embodiments, Filtering Module 320 may utilize an Absolute Distance Calculator 322 to compute absolute distances of data instances from Data Set 350 from their respective $K^{th}$ nearest neighbor. In some exemplary embodiments, the respective $K^{th}$ nearest neighbors may be provided by a k-NN Identifier 340. In some exemplary embodiments, the absolute distance computed by Absolute Distance Calculator 322 may be an Euclidian distance between the data instances and their respective $K^{th}$ nearest neighbor, a Hamming distance, or the like.

In some exemplary embodiments, K-NN Identifier 340 may be configured to identify the k nearest neighbors of each data point in Data Set 350. K-NN Identifier 340 may obtain a value of parameter k from User 395, from a record based on a default value, based on a computation that is based on the size of Data Set 350, or the like.

In some exemplary embodiments, Filtering Module 320 may utilize a Statistical Average Calculator 322 to compute a statistical average of absolute distances of all data instances in Data St 350, calculated by Absolute Distance Calculator 322. The statistical average may be a mean, a median, a mode or the like.

In some exemplary embodiments, Memory Unit 307 may comprise an Anomaly Detection Module 330. Anomaly Detection Module 330 may be configured to detect anomaly in Data Set 350 or similar data sets. In some exemplary embodiments Anomaly Detection Module 330 may be configured to classify a test data instance as normal or anomalous comparing to other data instances of Data Set 350. In some exemplary embodiments, Anomaly Detection Module 330 may be configured to perform on Data set 350 after being filtered by Filtering Module 320. In some exemplary embodiments, Anomaly Detection Module 330 may be configured to perform anomaly detection on Data Set 350 using an algorithm selected from the group of: LOF, ODIN, Connectivity Based Outlier Factor, or the like. In some exemplary embodiments, Anomaly Detection Module 330 may determine that the test data instance is abnormal if the relative density measurement is below a density threshold.

In some exemplary embodiments, Anomaly Detection Module 330 may utilize a Relative Density Calculator 332 to compute a relative density measurement of the test data instance. The relative density measurement may a number of data instances of Data Set 350 which the test data instance is one of their respective K nearest neighbors. Relative Density Calculator 332 may obtain the K nearest neighbors of each data instance from k-NN Identifier 340.

An Embodiment

In one exemplary embodiments of the disclosed subject matter, a distance-based method for anomaly detection, a density-based method for anomaly detection, and the hybrid method of FIG. 2 may be performed on a data set. The results of one embodiment in which each method was applied are represented in Tables 1, 2 and 3.

The data set which was examined comprised data from wearable devices that measure speed and acceleration associated with a change in movement. Acceleration and speed measurements have been performed by a number of volunteers for four activities: biking, driving, running and walking. Ten-second intervals have been used for activity detection. Each data point of the data set was used to represent an average of speeds and a variance of accelerations measured by a volunteer in a single activity.

Four experiments have been performed on the data. Each experiment applied the three methods of anomaly detection on a data set comprising data points from three activities, and a test data set comprising test data points from the four activities. Accordingly, test data points corresponding to the three activities are expected to be classified as normal, and test data points from the forth activity are expected to be classified as anomalous.

KNN classification was performed on the data, with k set to 3 and filtering threshold set to 4. Specificity, sensitivity and F1 score of results of the distance-based method on the four experiments are represented in Table 1.

TABLE 1

Summary of K-NN results

| | Goodness-of-fit (%) | | | |
|---|---|---|---|---|
| | Biking | Driving | Running | Walking |
| Specificity | 95.32 | 96.46 | 97.11 | 96.47 |
| Sensitivity | 93.52 | 95.83 | 56.71 | 65.59 |
| F1 score | 93.40 | 96.49 | 67.64 | 76.75 |

Sensitivity and specificity are statistical measures of the performance of classification method. Sensitivity may measure a proportion of positives that are correctly identified as such (i.e., a percentage of data points that were correctly identified as normal data points). Specificity may measure a proportion of negatives that are correctly identified as such (i.e., a percentage of data points that were correctly identified as anomalous). The F1 score may be a measure of the experience accuracy, which considers both precision (a number of correct positive results divided by a number of all positive results) and recall (a number of correct positive results divided by a number of positive results that should have been returned) of the experiment to compute the score. The F1 score may be interpreted as a weighted average of the precision and recall, where an F1 score may reach its best value at 1 (100%) and worst at 0 (0%).

A relative density method for anomaly detection was also used on the data set. The relative density method which was sued utilized the ODIN algorithm to compute anomaly scores of the data points. The k value of the ODIN algorithm was selected to be 20 and the density threshold was set to 7.

Specificity, sensitivity and F1 score of results of the relative density method on the four experiments are represented in Table 2.

TABLE 2

Summary of relative density method

| | Goodness-of-fit | | | |
|---|---|---|---|---|
| | Biking | Driving | Running | Walking |
| Specificity | 94.11 | 95.78 | 97.03 | 95.08 |
| Sensitivity | 87.72 | 85.96 | 89.63 | 81.04 |
| F1 score | 89.41 | 90.81 | 89.23 | 85.99 |

The hybrid method of FIG. 2 was also performed on the data set, during which data set were filtered based on the KNN approach and anomaly classification was performed on the test dataset based on the relative density algorithm used above.

Specificity, sensitivity and F1 score of results of the hybrid method on the four experiments are represented in Table 3.

TABLE 3

Summary of hybrid method

| | Goodness-of-fit | | | |
|---|---|---|---|---|
| | Biking | Driving | Running | Walking |
| Specificity | 92.33 | 94.06 | 94.62 | 92.86 |
| Sensitivity | 95.14 | 96.83 | 94.51 | 91.57 |
| F1 score | 92.28 | 96.09 | 87.94 | 90.49 |

The average F1-score of the four experiments may be used to compare the three different methods.

An average F1 score of F1 scores of the four experiments of each method is represented in Table 4.

TABLE 4

Comparison between average F1 scores

| Method | K-NN | Relative density | Hybrid |
|---|---|---|---|
| Average F1 score | 83.57 | 88.86 | 91.70 |

According to the average F1 scores, the hybrid method provides the best results, with an average F1-score 91.70. Hence, one effect of the disclosed subject matter may be to improve accuracy and precision of anomaly classification.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A computer-implemented method comprising:
    obtaining a data set and a test data point, wherein the data set comprises a plurality of data points corresponding to sensor data in a wearable device, wherein the data set comprises the test data point to be classified as normal or anomalous;
    normalizing the data set based on transforming the data points into values with a mean of zero and a standard deviation of one;
    filtering the normalized data set based on an absolute distance criterion to obtain a filtered data set comprising at least one data point, the filtering based on a ratio between an absolute distance of the test data point from k nearest neighboring data points and a statistical average of absolute distances of the data points from their respective nearest neighbors in the data set, wherein k corresponds to a square root of a number of the data points in the data set;
    performing anomaly classification on the test data point and the filtered data set, wherein the anomaly classification is based on a relative density criterion determined via a density-based spatial clustering of applications with noise (DBSCAN) technique;
    outputting an outcome of the anomaly classification; and
    modifying, based on the outcome, the wearable device to identify an activity performed by a user.

2. The computer-implemented method of claim 1, wherein the absolute distance criterion is based on an algorithm selected from the group of: a K-nearest neighbor (KNN) based algorithm, a hypergraph-based algorithm.

3. The computer-implemented method of claim 1, wherein the relative density criterion is based on an algorithm selected from the group of: Local Outlier Factor (LOP), Outlier Detection using Indegree Number (ODIN), Connectivity Based Outlier Factor (COP), Multi-Granularity Deviation Factor (MGDF), and Probabilistic Suffix Trees (PST).

4. The computer-implemented method of claim 1, wherein the data set is an unsupervised data set.

5. The computer-implemented method of claim 1, wherein prior to performing said anomaly classification on the test data point, adding the test data point to the filtered data set.

6. The computer-implemented method of claim 1, wherein the sensor data comprises data from the wearable device indicating a measurement of speed and acceleration associated with a change in a movement of the user.

7. The computer-implemented method of claim 1, wherein the activity comprises biking, driving, running, or walking.

8. A computerized apparatus having a processor, the processor being adapted to perform the steps of:
    obtaining a data set and a test data point, wherein the data set comprises a plurality of data points corresponding to sensor data in a wearable device, wherein the data set comprises the test data point to be classified as normal or anomalous;
    normalizing the data set based on transforming the data points into values with a mean of zero and a standard deviation of one;
    filtering the normalized data set based on an absolute distance criterion to obtain a filtered data set comprising at least one data point, the filtering based on a ratio between an absolute distance of the test data point from k nearest neighboring data points and a statistical average of absolute distances of the data points from their respective nearest neighbors in the data set, wherein k corresponds to a square root of a number of the data points in the data set;
    performing anomaly classification on the test data point within the filtered data set, wherein the anomaly classification is based on a relative density criterion determined via a density-based spatial clustering of applications with noise (DBSCAN) technique;
    outputting an outcome of the anomaly classification; and
    modifying, based on the outcome, the wearable device to identify an activity performed by a user.

9. The computerized apparatus of claim 8, wherein the absolute distance criterion is based on an algorithm selected from the group of: a K-nearest neighbor (KNN) based algorithm, a hypergraph-based algorithm.

10. The computerized apparatus of claim 8, wherein the relative density criterion is based on an algorithm selected from the group of: Local Outlier Factor (LOP), Outlier Detection using Indegree Number (ODIN), Connectivity Based Outlier Factor (COP), Multi-Granularity Deviation Factor (MGDF), and Probabilistic Suffix Trees (PST).

11. The computerized apparatus of claim 8, wherein the data set is an unsupervised data set.

12. The computerized apparatus of claim 8,
wherein prior to performing said anomaly classification on the test data point, adding the test data point to the filtered data set.

13. A computer program product comprising a computer readable storage medium retaining program instructions, which program instructions when read by a processor, cause the processor to perform a method comprising:
obtaining a data set and a test data point, wherein the data set comprises a plurality of data points corresponding to sensor data in a wearable device, wherein the data set comprises the test data point to be classified as normal or anomalous;
normalizing the data set based on transforming the data points into values with a mean of zero and a standard deviation of one;
filtering the normalized data set based on an absolute distance criterion to obtain a filtered data set comprising at least one data point, the filtering based on a ratio between an absolute distance of the test data point from k nearest neighboring data points and a statistical average of absolute distances of the data points from their respective nearest neighbors in the data set, wherein k corresponds to a square root of a number of the data points in the data set;
performing anomaly classification on the test data point within the filtered data set, wherein the anomaly classification is based on a relative density criterion determined via a density-based spatial clustering of applications with noise (DBSCAN) technique;
outputting an outcome of the anomaly classification; and
modifying, based on the outcome, the wearable device to identify an activity performed by a user.

* * * * *